United States Patent [19]

Kliegis et al.

[11] Patent Number: 5,715,836
[45] Date of Patent: Feb. 10, 1998

[54] METHOD AND APPARATUS FOR PLANNING AND MONITORING A SURGICAL OPERATION

[76] Inventors: Ulrich Kliegis, Holtenauer Str. 273, D-24106 Kiel; Bernd Lundt, Beselerallee 30, D-24105 Kiel, both of Germany

[21] Appl. No.: 501,044
[22] PCT Filed: Feb. 15, 1994
[86] PCT No.: PCT/DE94/00157
  § 371 Date: Aug. 16, 1995
  § 102(e) Date: Aug. 16, 1995
[87] PCT Pub. No.: WO94/19758
  PCT Pub. Date: Sep. 1, 1994

[30] Foreign Application Priority Data

Feb. 16, 1993 [DE] Germany ............ 43 04 571.5

[51] Int. Cl.$^6$ ........................................ A61B 19/00
[52] U.S. Cl. ................................................. 128/898
[58] Field of Search ............................. 128/630, 898

[56] References Cited

PUBLICATIONS

Hemler et al "Proceedings of Computer Based Medical Systems", IEEE Computer Society Press, New York, 14 Jun. 1992 pp. 309–314.

*Primary Examiner*—William E. Kamm
*Attorney, Agent, or Firm*—Foley & Lardner

[57] ABSTRACT

In a process for planning and monitoring a surgical operation, an operation site is established. At least one desired image of the operation site is generated from structural data which can be obtained by noninvasive means, and the planning is based on at least one section surface along which tissue is to be severed during the operation. An image of the planned section surface is then generated, which image is superposed during the operation on an actual image of the operation site or is projected onto the operation site itself. A three-dimensional desired image is used as the basis for planning the section surface. A three-dimensional image of the section surface is generated which is superposed on the desired image. It is created by computer-aided means from data taken from images generated in different ways. The images show the operation site in layers, each lying on & above the other. Computed tomography, nuclear magnetic resonance, ultrasound, and/or X-ray images of the operation site are evaluated when constructing the desired image. The desired image is stored as data record in the memory of a DPU. It is displayed on an image reproduction device for planning the operation. The image of the section surface is superposed on the desired image. It stands out visually from the desired image. The section surfaces are represented as transparent or semi-transparent lines.

59 Claims, 3 Drawing Sheets

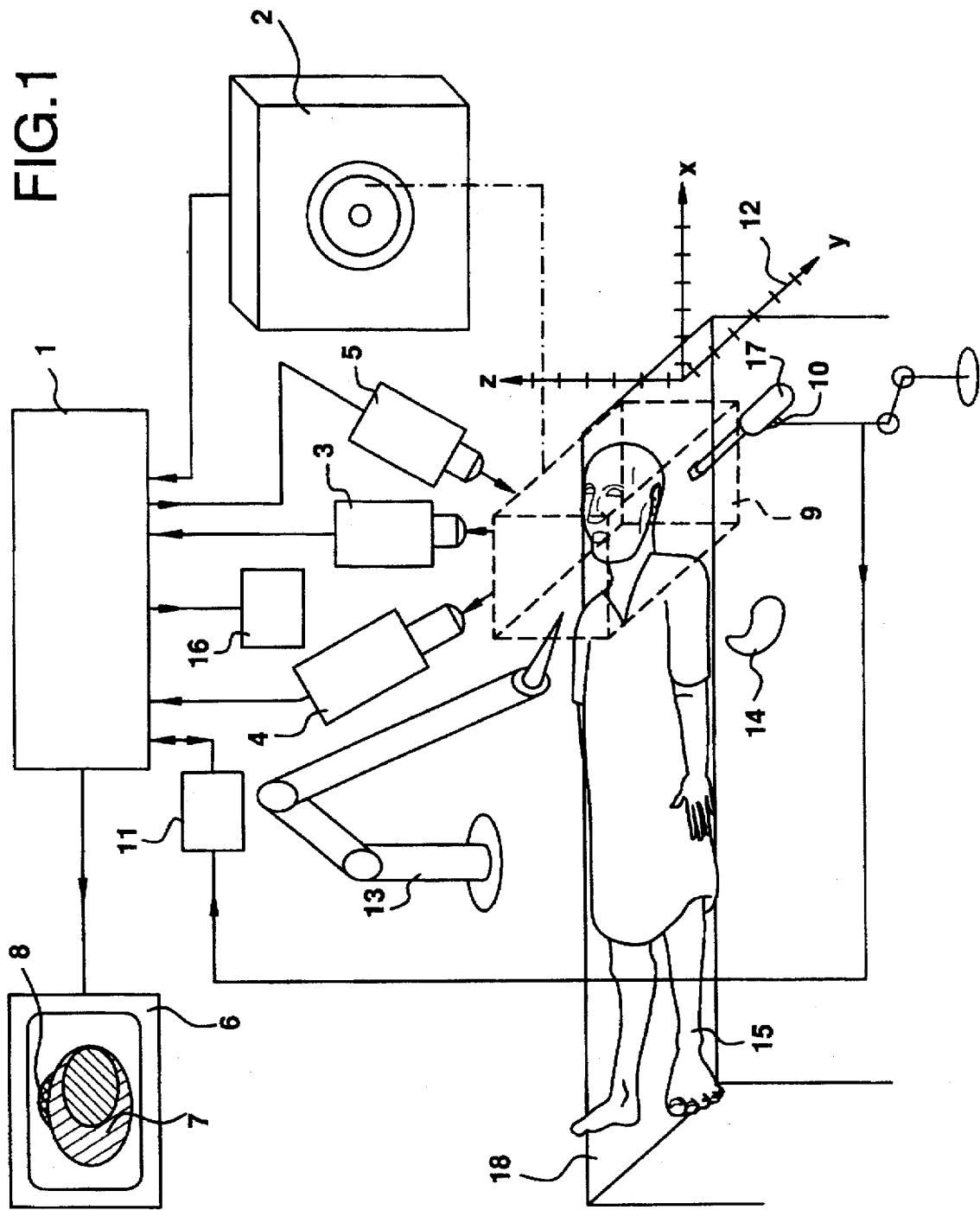

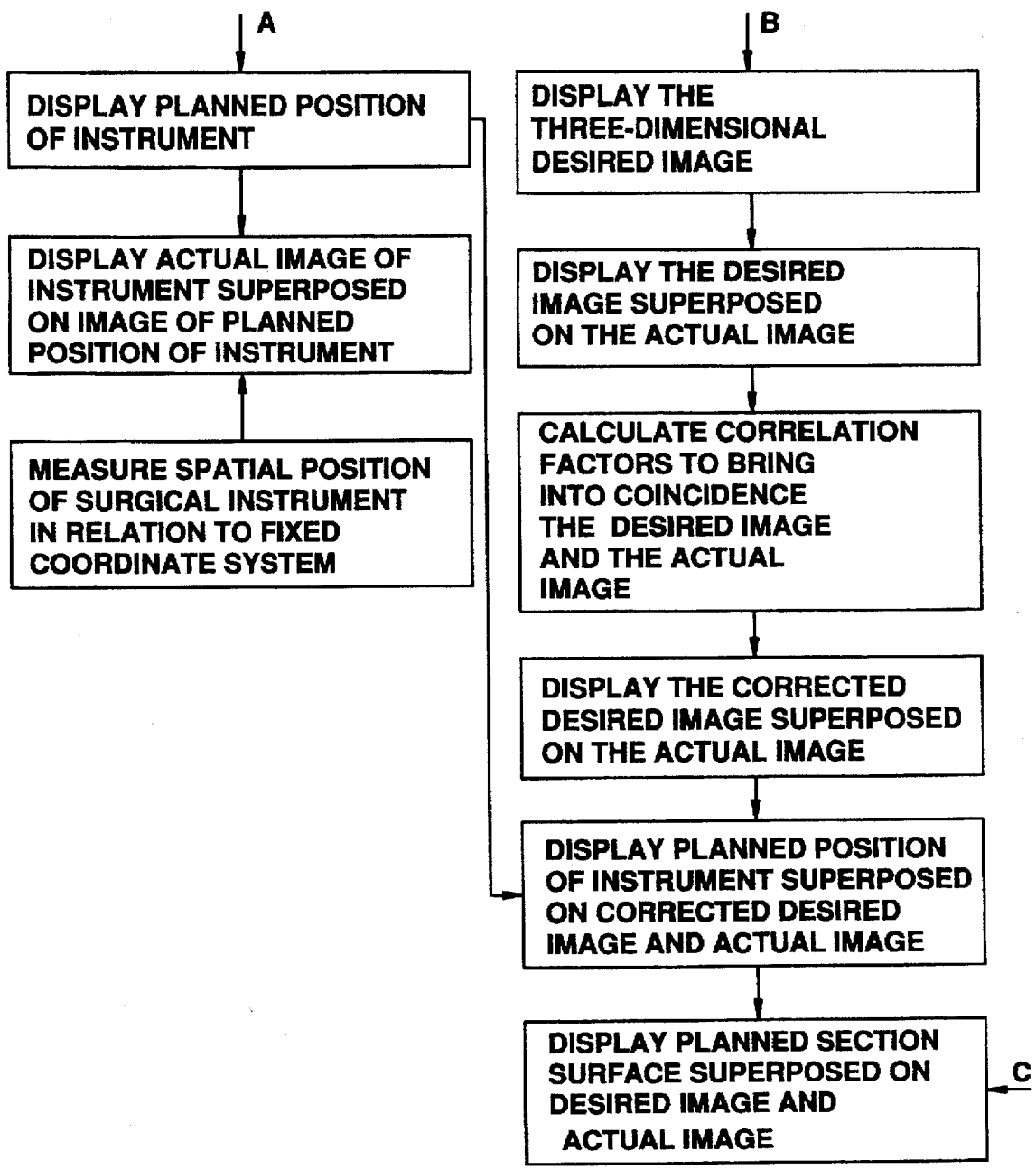

METHOD AND APPARATUS FOR PLANNING AND MONITORING A SURGICAL OPERATION

This application claims priority to PCT application Ser. No. PCT/DE94/00157, filed Feb. 15, 1994, published as WO94/19758 Sep. 1, 1994.

BACKGROUND OF THE INVENTION

The invention relates to a process for planning and monitoring a surgical operation, in which an operation site is established and at least one desired image of the operation site is generated from structural data which can be obtained by noninvasive means, and the planning is based on at least one section surface along which tissue is to be severed during the operation.

To prepare for complicated surgical operations, it is customary to plan the operating procedure in advance and to simulate the operation in order to establish theoretically the section surfaces at which the tissue is to be severed during the operation, a condition being that as little healthy tissue as possible should be removed and that vulnerable structures such as the larger vessels or nerves should as far as possible remain untouched. To this end, an operation site is first determined in general, and optimal section surfaces are determined on the basis of computed tomography, X-ray images, and other previously taken images of the operation site, and potential areas of risk in proximity to the section surfaces are discussed and marked on the images.

However, since the images on which the planning of the section surface is based are two-dimensional, transposition to three-dimensional relationships requires a great deal of experience and imagination. In addition, it is difficult to remember the often complex form of the section surfaces, so that the optimal section surfaces are in many cases deviated from inadvertently during the operation.

SUMMARY OF THE INVENTION

For this reason there is a need, particularly in the case of osteotomies, to be able to go back at any time during the operation to the previously planned section surfaces in order to make a comparison with the actual incision path and in order to avoid as far as possible inadvertent deviations from the planned section surfaces.

An object of the invention is to develop a process and a device of the type mentioned above, with which it is possible to obtain greater correspondence between a planned incision path and the incision made during the operation.

As regards the process, this object is achieved according to the invention in that an image of the planned section surface is generated. This image then is superposed during the operation on an actual image of the operation site or is projected onto the operation site itself. The invention thereby allows the surgeon to move a scalpel or another cutting tool in accordance with the preset visual information and to monitor his incision path on the basis of the image of the section surface.

BRIEF DESCRIPTION OF THE DRAWINGS

FIG. 1 is a schematic of an apparatus for providing information on anatomical relations and planned therapeutic measures in a body region in accordance with the invention; and FIGS. 2a and 2b are block diagrams illustrating a method for providing information on the anatomical relations and planned therapeutic measures in a body region.

DETAILED DESCRIPTION OF THE PREFERRED EMBODIMENTS

Figure 2A:
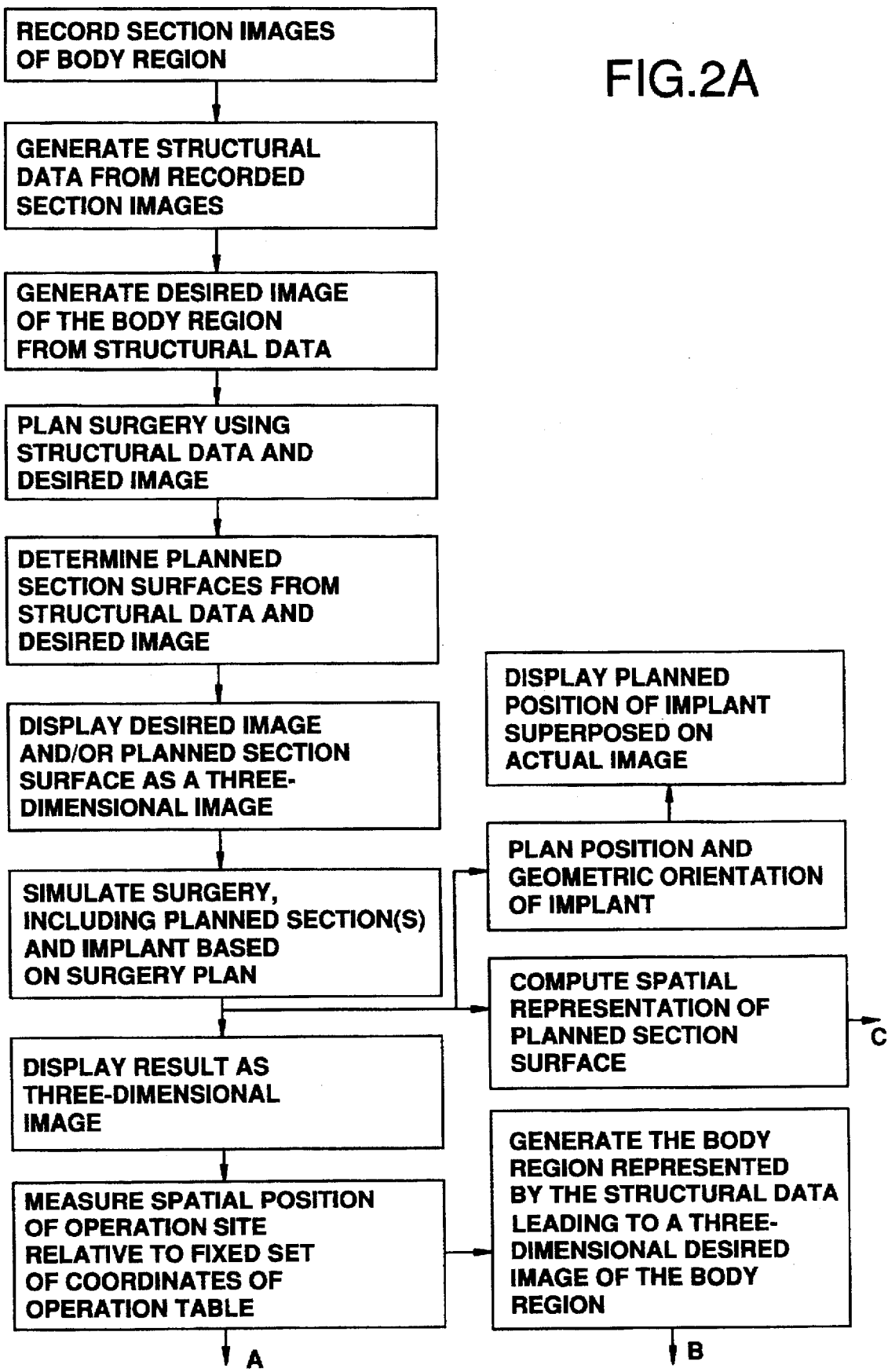

A preferred embodiment of invention proposes that, in contrast to the conventional processes for planning the section surface, a three-dimensional desired image is taken as a basis. The three-dimensional desired image is created from structural data by computer-aided means. The structural data is obtained by computer-aided means, for example by evaluating computed tomography, nuclear magnetic resonance, ultrasound, X-ray, or holographic examinations and by evaluating the sectional images which are thus made of the operation site. This three-dimensional desired image can be displayed on a monitor, for example. The three-dimensional (3-D) desired image makes it possible to plan the arrangement of the section surface over the entire depth of the operation site.

A further preferred embodiment of the invention proposes that a three-dimensional image of the section surface superposed on the desired image is generated on the monitor, for example, by inputting coordinates of points of the section surface. It is possible for optimization of this section surface to be effected by altering individual parameters, and it is possible for several section surface arrangements to be stored as a data record and to be recalled when needed. An advantageous embodiment of the invention proposes that the three-dimensional image of the section surface is stored as a 3D data record so that it too can be called up when needed.

The desired image together with the planned section surfaces, or only the section surfaces themselves, as well as lines indicating vulnerable structures, such as the larger vessels and nerves, can then be displayed during the operation in the field of vision of the surgeon, for example, on a monitor or a projector screen, or can be projected onto the operation site itself, to serve as a guideline and monitoring means when the surgeon makes incisions severing the tissue. However, if the desired image and the section surface are displayed on a monitor or on a projector screen, which guarantees clearer imaging compared to a projection on the operation site itself, a complete monitoring of the actual incision path is possible only if, as has been proposed according to the invention, an actual image of the operation site is superposed by this desired image, so that the surgeon, for example when cutting through tissue, can monitor in real time whether he is guiding his instrument along the planned section surface.

In order to guarantee a superpositioning of the section surface, desired image, and actual image, which is true to scale and correct in respect of the coordinates, a further preferred embodiment of the invention brings the section surface and/or the desired image into coincidence with the actual image by recording the operation site, for example with a video camera. The video image signal then is fed to an image processing unit, from which it is transmitted in the form of a data record to a data processing unit. The data record of the video image signal is compared in real time with the data record of the desired image in order to calculate correlation factors which permit compensation for coordinate shifts and/or scale differences. Subsequently, the desired image, which has been brought into coincidence with the actual image, is then displayed, superposed on the actual image, on the monitor. An interactive adaptation of the perspectives can also be effected manually.

The correlation of the desired image and actual image can be simplified in that, in accordance with an advantageous embodiment of the invention, the spatial position of the operation site is measured into a fixed system of coordinates before or during the operation, and the measurement data are input to the data processing unit.

Since the actual image of the operation site is also advantageously three-dimensional, like the desired image and the image of the section surface, in a display on a monitor or a projector screen, a further preferred embodiment of the invention generates stereoscopic images of the operation site for the actual image. The stereoscopic images allow the surgeon, who is equipped with special glasses, to see the actual image in three dimensions. Such a stereoscopic representation can be generated, for example, by means of the operation site being recorded by two video cameras which are arranged alongside one another, the image from one or other camera being shown alternately in rapid succession on the monitor or the projector screen. The stereoscopic representation is synchronously controlled. LCD glasses, in which the field of vision of each eye is in each case blocked alternately in the same sequence, allow the surgeon to see the actual image of the operation site as a three-dimensional stereo image.

When the desired image and the section surface are projected directly onto the operation site, these can be displayed in a similar manner on the operation site as a stereoscopic projection, for example by superposition of two curve paths generated by appropriately deflected laser beams or with the aid of video projection tubes. Thus, using special glasses, the direction of the section surface into the depth of the tissue can be rendered visually observable. The surgeon can then guide his scalpel or another cutting instrument directly along the three-dimensionally displayed section surface. In the last-mentioned case, it is also possible, for example, to choose an anaglyphic representation for the desired image, a red/green image of the desired image and of the section surface being superposed on the operation site. The red/green image appears as a stereoscopic image when viewed through corresponding red/green glasses.

For both the desired image and the image of the section surface, a representation is advantageously chosen from a direction which corresponds substantially to the direction of viewing of the surgeon during the operation. A further possibility consists in showing the desired image and the section surface constantly as a plan view from above, since the image is then independent of the position of the surgeon with respect to the operation site.

A further advantageous embodiment of the invention proposes that the position of the instrument guided by the surgeon during the operation is determined continuously and is compared with the position of the section surface in the desired image which has been brought into coincidence with the actual image. Deviations of the instrument from the planned section surface can be communicated to the surgeon, for example, by an acoustic or optical signal, whereupon he can correct the incision path, if so desired. As an alternative to indicating the deviation, the movement of the instrument along the planned section surface can also be assisted by an instrument guide controlled from the data processing unit. The instrument guide, in the event of deviations in the actual position of the instrument from the desired position, provides an appropriately calculated force counter to the force exerted by the surgeon on the instrument. This causes the instrument to return to the planned section surface or keeps the instrument within a predetermined range of tolerance with respect to the section surface. The action of the instrument guide can expediently be controlled in terms of its effect, so that the surgeon can react quickly to an operation which proceeds differently than the simulated operation.

As regards the device, invention preferably includes at least one data processing unit (DPU). The DPU may generate at least one desired image of the operation site from previously obtained structural data. The desired image of the operation site can be stored together with at least one section surface planned on the basis of the desired image, along which section surface tissue is to be severed during the operation. The invention also preferably includes at least one image reproduction device for projection of the section surface and/or of the desired image onto the operation site during the operation. In order to bring the desired image into exact coincidence with the operation site itself, a preferred embodiment of the invention includes a device for measuring the operation site. It is possible for the measurement data of that device to be input into the DPU in order to effect a correlation of scale and coordinates of the desired image and of the operation site.

Alternatively, the invention may include a device which comprises at least: one imaging device for producing a preferably continuous actual image of the operation site; DPU from which at least one desired image of the operation site can be generated from previously obtained structural data, stored together with at least one section surface planned on the basis of the desired image, and brought into coincidence with the actual image; and at least one image reproduction device for the display of the section surface and/or of the desired image superposed on the actual image. An advantageous embodiment of the invention further includes a device for inputting coordinates, for example a scanner, of at least one section surface represented superposed on the desired image.

An image processing unit is expediently connected to the imaging device. The image processing unit converts the recorded image of the operation site into electronic data which is transmitted to the DPU, where it is compared with the data record of the desired image in order to bring the desired image and the section surface into coincidence with the actual image with regard to the origin of the coordinates, the direction of the axes of the coordinates, and the scale.

A device in accordance with an embodiment of the invention is shown in FIG. 1. Here, a patient 15 is shown lying on a table 18. The operating site 9 is shown in phantom, and an implant is labeled 14. A coordinate system 12 enables measurement of different anatomical relations of the patient. The device includes a DPU 1 that may receive data from a CT 2, a video camera 3, and/or a microscope 4. The device may also include an image projection device 5 and a monitor 6 capable of displaying an actual image 7 of a body region of the patient and a desired image 8 of the body region. The device may further include an instrument guide 10, an alarm signal device 11, a measurement device 13, a microscope projection unit 16, and a surgical instrument 17. The device operates according to the methods and processes described herein.

A further advantageous embodiment of the invention includes at least two imaging devices for recording stereoscopic actual images of the operation site, which can be superposed by a three-dimensional image of the section surface and/or a three-dimensional desired image.

According to a further advantageous embodiment of the invention, the image reproduction device is designed as a monitor and is arranged in the field of vision of the surgeon during the operation.

The invention is explained in greater detail hereinafter with reference to an illustrative embodiment.

To plan and prepare for a surgical operation for removing a tumor from a human cranium, a series of sectional images of the cranium is first produced with the aid of computed tomography and/or nuclear magnetic resonance tomography. The images in each case show one layer, and the layers lie parallel and at a short distance one above the other. The measurement data determined by tomography is conveyed to a DPU 1, where, after an operation site has been established, a three-dimensional desired image of said site 8, i.e. of the cranial region presenting the tumor, is created from the measurement data by appropriate software. In addition, further structural data obtained, for example, by evaluating the results of ultrasound, X-ray, or holographic examinations of the cranium can then be input into the DPU.

The three-dimensional image 8 of the operation site is then displayed as graphics on a monitor 6 and serves as a basis for planning and simulating the operation.

In planning the operation, the results of the aforementioned examinations are taken into consideration when determining the pathologically altered parts of the brain and establishing section surfaces at which the tissue is to be severed during the operation. The section surfaces are in this case established in such a way that, on the one hand, as little healthy tissue as possible is removed, and, on the other hand, as few as possible of the larger vessels are damaged. In order to achieve the latter, vessels lying in proximity to the section surface are brought out by colors in the three-dimensional desired image 8 or are distinguished by indicator lines.

In order to represent the section surfaces themselves superposed on the desired image 8, coordinates of the section surface can be determined, for example, in a system of coordinates superposed on the desired image on the monitor 6. By inputting the coordinates into the DPU 1, the section surfaces can be emphasized by color or can be included as transparent or translucent surfaces in the desired image 8, in which case, however, a data record is also expediently created which contains exclusively the section surfaces in the scale and in the system of coordinates of the desired image.

A further possibility for inputting the section surfaces consists in breaking down the three-dimensional image of the operation site into two-dimensional sectional images. Not only plane, but also curved, section surfaces can be input in this case. A linear curve path is then input into the two-dimensional sectional images in each case with a graphics input medium, such as, for example, a graphics tablet, which linear curve path reproduces the section surface in the corresponding sectional image. A three-dimensional section surface image superposed on the desired image 8 can then be constructed again from the sum of the input section lines.

In order to achieve an optimal incision path, the three-dimensional desired image 8 can, for example, be rotated spatially and areas can be enlarged or made smaller.

After the planning of the operation has been completed, the 3D data record of the desired image 8 and of the image of the section surfaces are stored. It is possible for the section surfaces expediently to be stored broken down into individual surface elements which can be called up both separately and also jointly.

Before the start of the actual operation, the head of the patient 15 is secured against displacement in all directions on a support under a surgical microscope 4 and is measured in relation to a stationary system of coordinates 12 of the support, the spatial coordinates of specific characteristic points of the cranium being defined.

These coordinate points are input to the DPU 1, and correlation factors are calculated in order to bring the system of coordinates of the desired image and of the section surfaces into coincidence with the stationary system of coordinates 12 of the support.

Sensors arranged on the surgical microscope 4 determine the direction of viewing through the microscope 4 onto the operation site, and also the magnification set in each case, and transmit the sensed data to the DPU.

A corrected desired image and a corrected image of the section surfaces are then constructed from this data. The corrected images correspond, in terms of the origin of their coordinates, the directions of the axes of the coordinates, the scale, and the direction of viewing, exactly to the actual image 7 which can be seen in the eyepiece of the surgical microscope 4.

The corrected image of the section surfaces or the corrected desired image can then be reflected into the optical path of the surgical microscope 4 in such a way that it is superposed on the actual image 7 which can be seen in the eyepiece. The corrected desired image and the corrected image of the section surfaces can in this case be displayed on an image reproduction device 5, and the reproduced image can then be reflected into the optical path of the surgical microscope 4 in such a way that, superposed on the actual image 7, it impinges through the eyepiece onto the eye of the surgeon.

In the case of a surgical microscope 4 designed as a stereomicroscope, two corrected desired images and corrected images of the section surface can accordingly be generated which correspond to the direction of viewing through each of the eyepieces. By reflecting the corrected images into the respective eyepiece, a stereoscopic desired image or a stereoscopic representation of the section surfaces can be superposed on the stereoscopic actual image of the operation site, the direction of the section surfaces or of elements of the section surface being optically visible into the depth of the tissue structure. Accordingly, the surgeon can then position and move his instrument 17 in the operation site in accordance with the visual information displayed.

The monitoring of the incision path can be still further improved by recording continuously that the operation site visible through the eyepiece of the surgical microscope 4 using a video camera 3. The recorded images are fed in real time to an image processing unit, the data being fed from the output of the image processing unit to the DPU 1 and, there, being compared continuously with the image of the section surfaces. In the event of deviations of the surgical instrument 17 from the previously planned section surface, the surgeon can then be alerted to the deviations by an optical or acoustic alarm signal. Moreover, an instrument guide 10 controlled in real time from the DPU 1 can aid in guiding the instrument used by the surgeon. The instrument guide 10 leaves the execution of all movements to the surgeon, but limits him to courses of movement which correspond, with certain tolerances, to the planned incision path.

The instrument guide 10 can in this case be acted upon, for example via a servomechanism with electrical, pneumatic, or hydraulic actuation, with a component of force which varies according to the extent of the deviations and which is counter to the cutting force component exerted by the surgeon.

This process has particular importance in resection of diseased bone areas into which a prefabricated individual implant 14 is subsequently to be inserted. The geometrical data of the interfaces of the implant with respect to the bone represents the section surfaces which have to be produced by the osteotomy. The geometrical data may be obtained by producing the implant by a process using CAD or by scanning the surface of the implant.

What is claimed is:

1. A method for providing information on the anatomical relations and planned therapeutic measures in a body region, comprising:

generating section images of the body region;

generating a desired image of the body region from the section images of the body region;

determining at least one section surface of the body region; and displaying at least one of the desired image and an image of the at least one section surface superposed on an actual image of the body region.

2. A method for planning and monitoring a surgical operation, comprising:

determining an operation site;

obtaining structural data representing the operation site;

generating a desired image of the operation site from the structural data;

determining from the desired image a planned section surface along which tissue is to be severed during the operation;

displaying at least one of the desired image and an image of the planned section surface superposed on at least one of an actual image of the operation site or the operation site itself.

3. The method according to claim 2, wherein the desired image comprises a three-dimensional desired image, and the planned section surface is determined from the three-dimensional desired image.

4. The method according to claim 3, wherein the planned section surface comprises a three-dimensional planned section surface, and the image of the three-dimensional planned section surface is superposed on the three-dimensional desired image.

5. The method according to claim 3, further comprising:
providing a data processing unit; and
storing the image of the three-dimensional planned section surface as a three-dimensional data record in the data processing unit.

6. The method according to claim 2, wherein the structural data comprises structural data obtained by computer imaging techniques.

7. The method according to claim 6, wherein the structural data represents a plurality of layers of the operation site, the plurality of layers lying one above another.

8. The method according to claim 6, wherein the structural data comprises data obtained by at least one of computed tomography, nuclear magnetic resonance imaging, and x-ray imaging of the operation site, and the step of generating a desired image of the operation site comprises evaluating the structural data.

9. The method according to claim 2, further comprising:
providing a data processing unit; and
storing the desired image as a data record in the data processing unit.

10. The method according to claim 9, further comprising:
providing an image processing unit;
transmitting the structural data to the image processing unit;
converting the structural data to a data record of the operation site;
transmitting the data record of the operation site to the data processing unit; and comparing the data record of the desired image with the data record of the operation site.

11. The method according to claim 2, further comprising:
providing an image reproduction device; and
displaying the image of the planned section surface on the image reproduction device.

12. The method according to claim 2, further comprising:
providing an image reproduction device; and
displaying the desired image on the image reproduction device.

13. The method according to claim 12, further comprising:
displaying the image of the planned section surface superposed on the desired image.

14. The method according to claim 13, wherein the image of the planned section surface visually differs from the desired image.

15. The method according to claim 14, wherein the image of the planned section surface comprises an image displayed by at least one of a transparent line and a semi-transparent line, and the desired image comprises an image displayed by solid lines.

16. The method according to claim 2, further comprising:
providing a data processing unit; and
storing the image of the planned section surface as a data record in the data processing unit.

17. The method according to claim 2, further comprising:
bringing the image of the planned section surface into coincidence with the actual image.

18. The method according to claim 2, further comprising:
providing a surgical microscope, an image processing unit, and a data processing unit;
obtaining the actual image representing the operation site via the surgical microscope;
transmitting the actual image from an optical path of the surgical microscope to the image processing unit;
converting the actual image to a data record;
transmitting the data record to the data processing unit; and
displaying the desired image superposed on the actual image.

19. The method according to claim 18, wherein the actual image representing the operation site is transmitted continuously to the image processing unit.

20. The method according to claim 2, further comprising:
providing at least one video camera, an image processing unit, and a data processing unit;
obtaining structural data representing the operation site by recording the operation site via the at least one video camera;
transmitting the recorded structural data to the image processing unit;
converting the recorded structural data to a data record; and
transmitting the data record to the data processing unit.

21. The method according to claim 20, wherein the recorded structural data representing the operation site is transmitted continuously to the image processing unit.

22. The method according to claim 20, wherein the at least one video camera includes at least two video cameras arranged alongside each other, and the method further comprises generating stereoscopic images of the operation site via the at least two video cameras.

23. The method according to claim 2, further comprising:
measuring the spatial position of the operation site in a fixed system of coordinates prior to the operation.

24. The method according to claim 23, further comprising:
providing at least one surgical instrument; and
measuring continuously the spatial position of the at least one surgical instrument in relation to the fixed system of coordinates of the operation site.

25. The method according to claim 24, further comprising:
activating an alarm signal in the event of a deviation of the at least one surgical instrument from the planned section surface.

26. The method according to claim 24, further comprising:
providing an instrument guide and a data processing unit; and
guiding the at least one surgical instrument along the planned section surface by controlling the instrument guide via the data processing unit.

27. The method according to claim 23, further comprising:
providing at least one surgical instrument; and
measuring intermittently the spatial position of the at least one surgical instrument in relation to the fixed system of coordinates of the operation site.

28. The method according to claim 27, further comprising:
activating an alarm signal in the event of a deviation of the at least one surgical instrument from the planned section surface.

29. The method according to claim 28, further comprising:
providing an instrument guide and a data processing unit; and
guiding the at least one surgical instrument along the planned section surface by controlling the instrument guide via the data processing unit.

30. The method according to claim 2, further comprising:
determining coordinate systems for the desired image, the image of the planned section surface, and the actual image, respectively;
calculating correlation factors to bring into coincidence the coordinate systems of the desired image and the actual image, resulting in a corrected desired image.

31. The method according to claim 30, further comprising:
calculating correlation factors to bring into coincidence the coordinate systems of the planned section surface and the actual image, resulting in a corrected image of the planned section surface.

32. The method according to claim 31, further comprising:
providing a surgical microscope; and
reflecting the corrected image of the planned section surface into an optical path of the surgical microscope.

33. The method according to claim 32, further comprising:
projecting the corrected image of the planned section surface onto the operation site.

34. The method according to claim 32, further comprising:
generating a stereoscopic image of the corrected image of the planned section surface.

35. The method according to claim 31, further comprising:
providing an image reproduction device; and
displaying the corrected image of the planned section surface superposed on the actual image via the image reproduction device.

36. The method according to claim 2, further comprising:
storing at least one line, indicating at least one of blood vessels or nerves, as a data record; and
displaying the data record superposed on the actual image.

37. The method according to claim 2, further comprising:
storing at least one line, indicating at least one of blood vessels or nerves, as a data record; and
projecting the data record on the operation site.

38. An apparatus for providing information on the anatomical relations and planned therapeutic measures in a body region, comprising:
a data processing unit adapted to collect structural data representative of a body region, adapted to generate a first data set representative of at least one desired image of the body region from the structural data, and adapted to generate a second data set representative of a planned section surface from the desired image;
a storage device adapted to store the first data set and the second data set; and
at least one image reproduction device adapted to display at least one of the desired image and an image of the planned section surface superposed on the body region.

39. An apparatus for planning and monitoring a surgical operation, comprising:
a data processing unit adapted to collect structural data representative of an operation site, adapted to generate a first data set representative of at least one desired image of the operation site from the structural data, and adapted to generate a second data set representative of a planned section surface from the desired image;
a storage device adapted to store the first data set and the second data set; and
at least one image reproduction device adapted to display at least one of the desired image and an image of the planned section surface superposed on the operation site.

40. The apparatus according to claim 39, further comprising:
a measurement device adapted to measure the operation site.

41. The apparatus according to claim 39, further comprising:
at least two video cameras for recording the operation site, the at least two video cameras electronically communicating with the at least one image reproduction device, which generates two images of the recorded operation site, the at least one image reproduction device displaying one image superposed on the other image in rapid succession.

42. The apparatus according to claim 39, further comprising:
a stereoscopic display unit adapted to be controlled in synchronism with the at least one image reproduction device.

43. The apparatus according to claim 39, further comprising:
a laser for projecting at least one of the desired image and the image of the section surface.

44. The apparatus according to claim 43, further comprising:

a deflection device electrically communicating with and controlled by the data processing unit, the deflection device adapted to deflect the projected image produced by the laser.

45. The apparatus according to claim 39, further comprising:

at least two video projection tubes for projecting at least one of the desired image and the image of the section surface.

46. An apparatus for planning and monitoring a surgical operation for the method .according to claim 23 comprising:

at least one imaging device adapted to produce a continuous actual image of an operation site;

a data processing unit adapted to collect structural data representative of the operation site, adapted to generate a first data set representative of the desired image of the operation site from the structural data, and adapted to generate a second data set representative of the planned section surface from the desired image;

a storage device adapted to store the first data set and the second data set; and at least one image reproduction device adapted to display at least one of the desired image and the image of the planned section surface superposed on the actual image.

47. The apparatus according to claim 46, wherein the storage device stores coordinates of the planned section surface superposed on the desired image.

48. The apparatus according to claim 46, wherein the at least the image reproduction device includes at least two imaging devices adapted to record a stereoscopic actual image of the operation site.

49. The apparatus according to claim 46, further comprising:

an image processing unit electrically communicating with the at least one image reproduction device.

50. The apparatus according to claim 46, wherein the at least one image reproduction device is arranged in the field of vision of a person performing the operation.

51. The apparatus according to claim 46, wherein the at least one image reproduction device comprises a monitor.

52. The apparatus according to claim 46, further comprising:

a surgical microscope; and a reflecting device for reflecting at least one of the desired image and the image of the planned section surface into an optical path of the surgical microscope.

53. The apparatus according to claim 46, further comprising:

at least one surgical instrument; and a measurement device coupled to the at least one surgical instrument and adapted to measure a coordinate position of the at least one surgical instrument relative to the operation site.

54. The apparatus according to claim 46, further comprising:

an instrument guide communicating with and controlled by the data processing unit; and at least one surgical instrument coupled to the instrument guide.

55. A method for planning and monitoring a surgical operation, comprising:

determining an operation site where an implant is to be inserted;

obtaining structural data representing the operation site;

generating a desired image of the operation site from the structural data;

determining a planned position and a spatial orientation of the implant;

storing at least the desired position and orientation of the implant as a data record;

producing a graphical representation of at least the desired position and orientation of the implant;

displaying the graphical representation superposed on an actual image of the operation site or projected onto the operation site so that the implant can be positioned to match at least the desired position and orientation thereof; and fixing the implant based on the graphical representation displayed.

56. The method according to claim 55, further comprising storing a geometrical configuration of the implant, wherein the geometrical configuration of the implant is superposed on the actual image of the operation site, thus transferring information representing a desired result of the operation.

57. The method according to claim 56, wherein the geometrical configuration of the implant is obtained using CAD.

58. The method according to claim 56, wherein the geometrical configuration of the implant is obtained by a three-dimensional surface scanner.

59. The method according to claim 56, wherein the implant includes a piece of tissue resected from a same or different individual.

* * * * *